United States Patent
Al Hasan et al.

(10) Patent No.: US 11,295,861 B2
(45) Date of Patent: Apr. 5, 2022

(54) EXTRACTED CONCEPT NORMALIZATION USING EXTERNAL EVIDENCE

(71) Applicant: KONINKLIJKE PHILIPS N.V., Eindhoven (NL)

(72) Inventors: Sheikh Sadid Al Hasan, Cambridge, MA (US); Yuan Ling, Somerville, MA (US); Oladimeji Feyisetan Farri, Yorktown Heights, NY (US); Vivek Varma Datla, Ashland, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 427 days.

(21) Appl. No.: 16/478,940

(22) PCT Filed: Jan. 25, 2018

(86) PCT No.: PCT/EP2018/051820
§ 371 (c)(1),
(2) Date: Jul. 18, 2019

(87) PCT Pub. No.: WO2018/141622
PCT Pub. Date: Aug. 9, 2018

(65) Prior Publication Data
US 2020/0043610 A1   Feb. 6, 2020

Related U.S. Application Data

(60) Provisional application No. 62/454,089, filed on Feb. 3, 2017.

(51) Int. Cl.
*G16H 50/20* (2018.01)
*G16H 50/70* (2018.01)
(Continued)

(52) U.S. Cl.
CPC ......... *G16H 50/20* (2018.01); *G06F 16/3329* (2019.01); *G06N 20/00* (2019.01); *G16H 50/70* (2018.01)

(58) Field of Classification Search
CPC ...... G06N 20/00; G06N 5/04; G06F 16/3329; G06F 16/334; G06F 16/3338; G06F 16/3322; G16H 50/20; Y10S 707/99933
See application file for complete search history.

(56) References Cited

U.S. PATENT DOCUMENTS 6,601,059 B1 * 7/2003 Fries ................. G06F 16/951
8,655,682 B2   2/2014 Srivastava et al.
(Continued)

OTHER PUBLICATIONS

Narasimhan, et al., "Improving Information Extraction by Acquiring External Evidence with Reinforcement Learning", Cornell University Library, Library Cornell University, NY, Mar. 25, 2016, 10 pages.
(Continued)

*Primary Examiner* — Eric J Yoon

(57) ABSTRACT

Various embodiments described herein relate to a method, system, and non-transitory machine-readable medium including one or more of the following: extracting a first concept from input data presented for processing by a downstream function; identifying external data from an external resource based on the first concept; extracting a second concept from the external data; revising the first concept based on the second concept to produce a revised concept, wherein revising includes: applying a machine learning agent to determine whether to keep the first concept or adopt the second concept, and adopting the second concept in place of the first concept for use as the revised concept based on a decision by the machine learning agent to adopt the second concept; and further processing the
(Continued)

revised concept according to the downstream function to generate an output.

14 Claims, 6 Drawing Sheets

(51) Int. Cl.
   *G06N 20/00* (2019.01)
   *G06F 16/332* (2019.01)

(56) References Cited

U.S. PATENT DOCUMENTS

| | | | |
|---|---|---|---|
| 9,002,773 B2 | 4/2015 | Bagchi et al. | |
| 9,690,938 B1* | 6/2017 | Saxe | G06N 3/0454 |
| 10,599,997 B2* | 3/2020 | Allen | G06N 5/02 |
| 2011/0004588 A1* | 1/2011 | Leitersdorf | G06F 16/951 |
| | | | 707/711 |
| 2012/0005219 A1* | 1/2012 | Apacible | G06F 16/334 |
| | | | 707/768 |
| 2012/0179705 A1* | 7/2012 | Kumaran | G06F 16/3325 |
| | | | 707/767 |
| 2016/0203281 A1 | 7/2016 | Zalis et al. | |
| 2017/0140290 A1* | 5/2017 | Block | G06N 5/02 |

OTHER PUBLICATIONS

Hasan, et al., "Clinical Question Answering using Key-Value Memory Networks and Knowledge Graph", Jun. 9, 2016, Retrieved from the Internet: URL:https://pdfs.semanti cscholar.org/7e0a/ dll9bba3201d97cd062c4eeab6d3553f20a2.pdf, 15 pages.

Tang, et al., "Inquire and Diagnose: Neural Symptom Checking Ensemble using Deep Reinforcement Learning", Jan. 1, 2016, 29th Conference on Neural Information Processing Systems (NIPS 2016), Barcelona, Spain, pp. 1-9.

Chali, et al., "A reinforcement learning formulation to the complex question answering problem", Information Processing and Management, vol. 51, No. 3, May 1, 2015, pp. 252-272.

Al Hasan, et al., "Complex Question Answering: Minimizing the Gaps and Beyond", Master of Science, University of Lethbridge, 2010, A Thesis Submitted to the School of Graduate Studies, Doctor of Philosophy, 202 pages.

Li, Y., "Deep Reinforcement Learning: an Overview", Jan. 26, 2017, Retrieved from the Internet: URL:https://arxiv.org/pdf/1701. 07274v2.pdf, pp. 1-30.

International Search Report and Written Opinion for International Application No. PCT/EP2018/051820, filed Jan. 25, 2018, 17 pages.

Johnson, et al., "Machine Learning and Decision Support in Critical Care", Proceedings of the IEEE, vol. 104, No. 2, Feb. 2016, pp. 444-466.

\* cited by examiner

EXTRACTED CONCEPT NORMALIZATION USING EXTERNAL EVIDENCE

CROSS REFERENCE TO RELATED APPLICATIONS

The present application is the U.S. National Phase application under 35 U.S.C. § 371 of International Application No. PCT/EP2018/051820, filed on Jan. 25, 2018, which claims the benefit of U.S. Provisional Application No. 62/454,089, filed on Feb. 3, 2017. These applications are hereby incorporated by reference herein in their entirety.

TECHNICAL FIELD

Embodiments described herein generally relate to artificial intelligence fields such as natural language processing, reinforcement learning, and expert systems. More particularly but not exclusively, various embodiments relate to systems and methods for inferring correct diagnoses using extracted data from texts and external resources.

BACKGROUND

Clinical decision making is a complex task that often requires significant medical background and investigation based on an underlying clinical scenario. For example, given a clinical case for a patient (e.g., the patient's past medical history, their symptoms, etc.), medical personnel may have to order appropriate medical tests and procedures, infer the correct diagnosis, and prescribe the best possible treatment plan. Medical personnel may base these decisions and actions on their prior knowledge and experience, and knowledge obtained through research of external resources.

Intelligent clinical decision support tools have been developed to support medical personnel with these steps. Specifically, these tools aim to improve the clinical decision making process by reducing the cognitive burden on medical personnel by automatically inferring the correct tests, diagnoses, and treatments given a particular medical case. However, due to the unavailability of a large annotated training corpus, it is often difficult to build effective models for intelligent clinical decision support.

Moreover, existing reinforcement learning techniques observe and learn from training data in a non-incremental fashion. These prior techniques may focus only on structured clinical data (e.g., physiological signals, vital signs, lab tests, and other variables). This may lead to failure in processing the ambiguities and uncertainties inherent to a complex clinical scenario.

In some scenarios, a patient may describe his or her symptom(s) in such a way that is not easily identified by automated techniques. For example, a patient may describe a particular ailment using certain words that do not match stored symptom descriptions and their associated diagnoses. Accordingly, a model may be unable to infer the correct diagnosis.

Existing techniques for diagnostic inferencing mostly rely on supervised classification models using various neural network architectures. However, these models heavily rely on large labeled data sets and may lack the ability to capture inherent ambiguities and complexities of a clinical scenario. Moreover, they are limited by the number of diagnosis labels and the use of medical codes to simplify the computational and linguistic difficulties of a clinical case.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

Various embodiments described herein relate to a method for normalizing input data against external data, the method including: extracting a first concept from input data presented for processing by a downstream function; identifying external data from an external resource based on the first concept; extracting a second concept from the external data; revising the first concept based on the second concept to produce a revised concept, wherein revising includes: applying a reinforcement learning agent to determine whether to keep the first concept or adopt the second concept, and adopting the second concept in place of the first concept for use as the revised concept based on a decision by the machine learning agent to adopt the second concept; and further processing the revised concept according to the downstream function to generate an output.

Various embodiments described herein relate to a system for normalizing input data against external data, the method including: a memory; and a processor configured to: extract a first concept from input data presented for processing by a downstream function; identify external data from an external resource based on the first concept; extract a second concept from the external data; revise the first concept based on the second concept to produce a revised concept, wherein revising includes: apply a machine learning agent to determine whether to keep the first concept or adopt the second concept, and adopt the second concept in place of the first concept for use as the revised concept based on a decision by the machine learning agent to adopt the second concept; and further process the revised concept according to the downstream function to generate an output.

Various embodiments described herein relate to a non-transitory machine-readable medium encoded with instructions for execution by a processor, the non-transitory machine-readable medium including: instructions extracting a first concept from input data presented for processing by a downstream function; instructions identifying external data from an external resource based on the first concept; instructions extracting a second concept from the external data; instructions revising the first concept based on the second concept to produce a revised concept, wherein revising includes: instructions applying a machine learning agent to determine whether to keep the first concept or adopt the second concept, and instructions adopting the second concept in place of the first concept for use as the revised concept based on a decision by the machine learning agent to adopt the second concept; and instructions further processing the revised concept according to the downstream function to generate an output.

Various embodiments are described wherein the input data is free text and the first concept is at least one of a term and a phrase extracted from the free text.

Various embodiments are described wherein identifying external data from an external resource based on the first concept includes executing a query including the first concept against the external resource.

Various embodiments are described wherein revising the first concept based on the second concept to produce a revised concept further includes: identifying additional external data from the external resource based on the second concept; extracting a third concept from the additional external data; applying the machine learning agent to determine whether to keep the second concept or adopt the third concept, and adopting the third concept in place of second first concept for use as the revised concept based on a decision by the machine learning agent to adopt the third concept.

Various embodiments are described wherein further processing the revised concept according to the downstream function to generate an output includes: executing a query including the revised concept against the external resource to retrieve a result; and presenting the result as the output.

Various embodiments additionally include training the machine learning agent including: calculating a reward value for use in training the machine learning agent by comparing the output to a ground truth associated with the input data.

Various embodiments are described wherein the machine learning agent includes a deep learning neural network including: an input layer that receives a state feature vector derived from the first concept and the second concept; and an output layer that presents a plurality of expected reward values respectively associated with each of a plurality of actions, wherein the machine learning agent is configured to select the action associated with the highest expected reward value.

In one aspect, embodiments relate to a method for inferring a patient's diagnosis. I various embodiment, the method includes receiving, using an interface, text describing a patient's state; extracting, using a concept extraction module, at least one initial concept from the received text; formulating, using a query formulation module, at least one query for submission to at least one external resource, wherein the at least one query is based on the at least one initial concept; extracting, using an evidence search module, at least one new concept from a response from the at least one external resource to the at least one query; generating, using a reinforcement learning module, at least one feature based on a comparison of the at least one initial concept and the at least one new concept; and training an agent associated with the reinforcement learning module using the at least one generated feature.

Some embodiments relate to a non-transitory machine-readable medium (e.g., a volatile or non-volatile memory) encoded with instructions for execution by a processor and for performing the above-described method.

In some embodiments, generating the at least one feature includes generating a state vector including a comparison between a set of initial concepts and a set of new concepts. In some embodiments, the state vector represents the similarity between the set of initial concepts and the set of new concepts.

In some embodiments, training the agent includes training the agent using a known correct diagnosis given a clinical scenario.

In some embodiments, training the agent includes optimizing a reward function that measures the accuracy of a candidate diagnosis.

In some embodiments, the method further includes supplying, using the agent, a clinical diagnosis to an administrator.

In some embodiments, formulating the query involves generating a semantically similar query using the at least one initial concept and a corpus of related medical concepts.

In some embodiments, the reinforcement module is implemented as a deep Q network. In some embodiments, the deep Q network optimizes a reward function concerning the accuracy of outputs, accuracy of extracted concepts, or human feedback.

In some embodiments, the agent includes an internal state including confidence values relating at least one concept to a clinical diagnosis.

According to another aspect, embodiments relate to a system for inferring a patient's diagnosis. In various embodiments, the system includes an interface for receiving text describing a patient's state; a concept extraction module executing instructions stored on a memory to extract at least one initial concept from the received text; a query formulation module executing instructions stored on the memory to formulate at least one query for submission to the at least one external resource, wherein the at least one query is based on the at least one initial concept; an evidence search module executing instructions stored on the memory to extract at least one new concept from a response from at least one external resource to the at least one query; and a reinforcement learning module executing instructions stored on the memory to: generate at least one feature based on a comparison of the at least one initial concept and the at least one new concept, and train an agent associated with the reinforcement learning module using the at least one generated feature.

In some embodiments, the reinforcement learning module generates the at least one feature by generating a state vector including a comparison between a set of initial concepts and a set of new concepts. In some embodiments, the state vector represents the similarity between the set of initial concepts and the set of new concepts.

In some embodiments, the agent is trained using a known correct diagnosis given a clinical scenario.

In some embodiments, the agent is trained by optimizing a reward function that measures the accuracy of a candidate diagnosis. In some embodiments, the agent is further configured to output a clinical diagnosis to an administrator.

In some embodiments, the query formulation module is configured to formulate the query by generating a semantically similar query using the at least one initial concept and a corpus of related medical concepts.

In some embodiments, the reinforcement learning module is implemented as a deep Q network. In some embodiments, the deep Q network optimizes a reward function concerning the accuracy of outputs, accuracy of extracted concepts, or human feedback.

In some embodiments, the agent includes an internal state including confidence values relating at least one concept to a clinical diagnosis.

According to yet another aspect, embodiments relate to a method for inferring a patient's diagnosis. In various embodiments, the method includes receiving, using an interface, text describing a patient's state; extracting, using a concept extraction module, at least one initial concept from the received text; formulating, using a query formulation module, at least one query for submission to at least one external resource, wherein the at least one query is based on the at least one initial concept; extracting, using an evidence search module, at least one new concept from a response from the at least one external resource to the at least one query; generating, using a reinforcement learning module implemented as a deep Q network that optimizes a reward function concerning the accuracy of outputs, accuracy of extracted concepts, or human feedback, at least one feature based on a comparison of the at least one initial concept and the at least one new concept; training an agent associated with the reinforcement learning module using the at least one generated feature; and supplying, using the agent, a clinical diagnosis to an administrator that is based on the at least one generated feature.

BRIEF DESCRIPTION OF DRAWINGS

Non-limiting and non-exhaustive embodiments of the invention are described with reference to the following figures, wherein like reference numerals refer to like parts throughout the various views unless otherwise specified.

DETAILED DESCRIPTION

Figure 1:
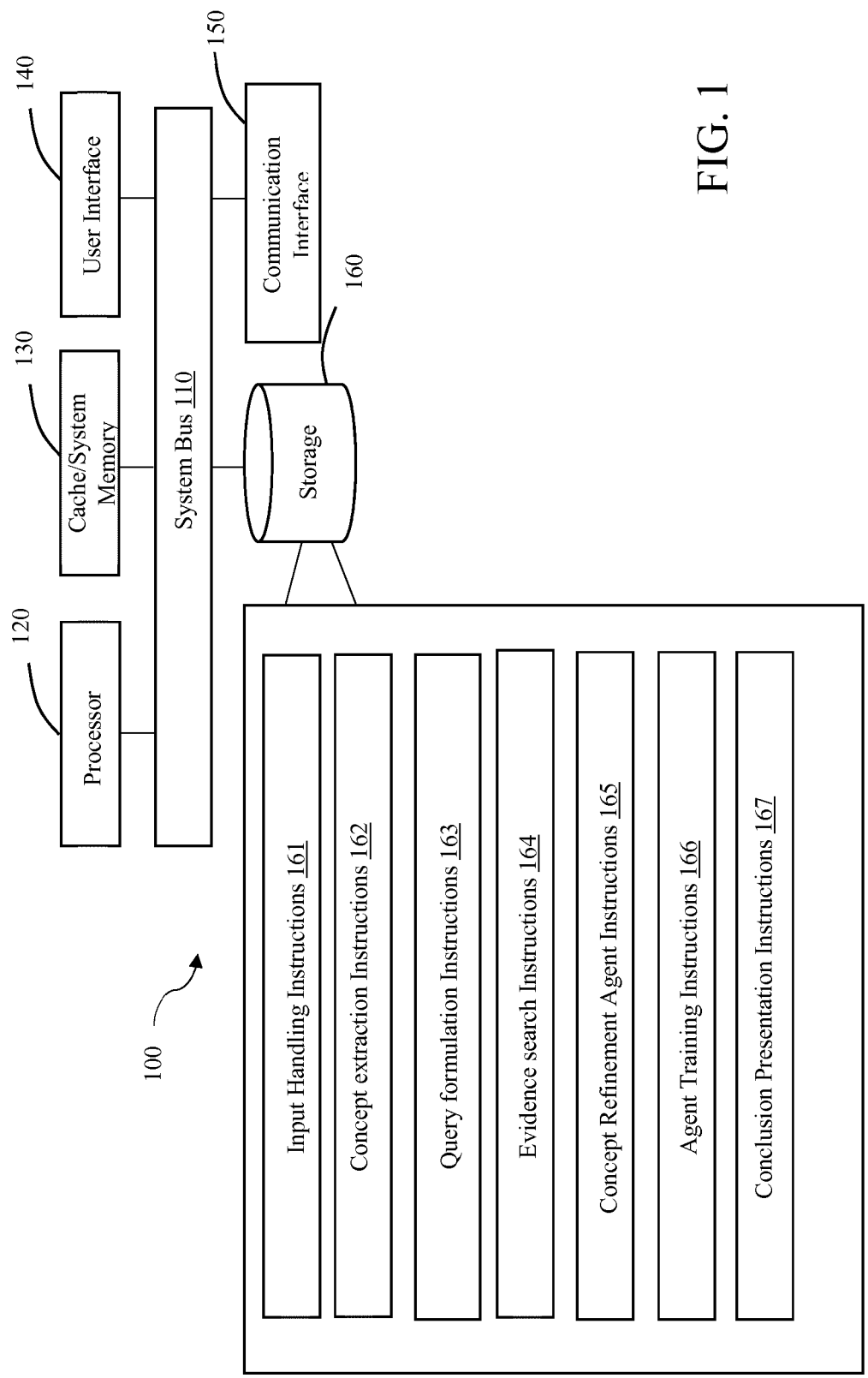
FIG. 1 illustrates a system for inferring a patient's diagnosis in accordance with one embodiment.

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment.

Some portions of the description that follow are presented in terms of symbolic representations of operations on non-transient signals stored within a computer memory. These descriptions and representations are used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices. Portions of the present disclosure include processes and instructions that may be embodied in software, firmware or hardware, and when embodied in software, may be downloaded to reside on and be operated from different platforms used by a variety of operating systems.

The present disclosure also relates to an apparatus for performing the operations herein. This apparatus may be specially constructed for the required purposes, or it may include a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each may be coupled to a computer system bus. Furthermore, the computers referred to in the specification may include a single processor or may be architectures employing multiple processor designs for increased computing capability.

The processes and displays presented herein are not inherently related to any particular computer or other apparatus. Various general-purpose systems may also be used with programs in accordance with the teachings herein, or it may prove convenient to construct more specialized apparatus to perform one or more method steps. The structure for a variety of these systems is discussed in the description below. In addition, any particular programming language that is sufficient for achieving the techniques and implementations of the present disclosure may be used. A variety of programming languages may be used to implement the present disclosure as discussed herein.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

Various embodiments of systems and methods described herein formulate the complex clinical decision making process as a sequential decision making process using deep reinforcement learning. Systems and methods described herein can infer the correct diagnosis, and therefore the appropriate tests and treatments, from unstructured free texts by autonomously investigating relevant external resources.

In other words, features of various embodiments described herein may rely on raw free-text clinical notes to infer the appropriate clinical concepts. From clinical notes, an agent can infer the most appropriate diagnoses, appropriate tests, and treatments for a patient by leveraging external resources.

Features of various embodiments described herein can be implemented in a variety of applications. For example, the systems and methods can be used by consumers and/or patients to obtain a general understanding of their healthrelated issues. Similarly, and as discussed previously, systems and methods described herein may assist medical personnel in treating patients.

According to the foregoing, various embodiments present systems for drawing a conclusion in a presented problem having a nature such that various concepts imply, to various extents, a particular conclusion. For example, in the realm of clinical diagnosis, the concepts may be symptoms that imply one or more particular diagnosis. In other words, a particular patient case may involve a list of symptoms and present the problem of diagnosing the patient. According to various embodiments, an agent may be trained to reference external resources (e.g., medical literature) to determine which entries of diseases or conditions list the presented symptoms, and are therefore most likely to represent a correct diagnosis for the present patient.

Some such agents may operate on the seemingly simple approach of extracting the relevant concepts from the problem statement and searching the knowledge base for conclusions that are associated with those concepts. The located entries with the greatest degree of overlap with the concepts are ranked as the most likely correct conclusions. In practice, however, implementation of this approach is non-trivial. Identification of the meaningful concepts in the problem statement is a formidable task in and of itself within the realm of natural language processing (NLP). Many such solutions rely on the use of ontologies, where the concepts are defined according to a standardized structure; in such a case, cross referencing to the knowledge base of evidence with the extracted ontological concepts is relatively simple because a "match" is as simple as determining whether the same ontological concept is listed in the evidence entry. However, many applications cannot rely, at least fully, on the use of ontologies (e.g., those utilizing free text as the problem statement or the evidence entries, and where the free text includes terms and phrases beyond the coverage of the ontologies). As such, concepts extracted from the problem statement may not be easily matched to those in the evidence entries due to, e.g., the difficulty in identifying which concepts are meaningful in the problem statement or use of synonyms or related concepts between the two sets of information.

Accordingly, various embodiments present an agent system and method for training such that it adapts the concepts initially extracted from the problem statement. In particular, the agent may begin by extracting a set of concepts from the problem statement and then proceed to refine that concept set against the evidence pool, before using the concepts to draw ultimate conclusions (e.g., again using the evidence pool). For example, the agent may first extract concepts C1, C2, and C3 from the problem statement, search the evidence pool for the most relevant entry to that set, and then determine based on that entry that concept C4 is actually better than C3 for the purpose of reaching a conclusion. In the clinical setting, for example, the agent may determine that, while "high temperature" was written in the patient's medical record, the term "fever" may be a better search term to be used in the future based on its use in the first obtained evidence entry. After updating the concept list, the agent may search the evidence pool again using the new concepts. Such process may continue until the agent is satisfied with the concepts, which may then be used to perform a final search (which may be the same type of search as the previous searches, may construct the query in a different manner, or may search against a different source) to locate one or more conclusions to be drawn from the final concept list. Thus, the agent first adapts the initial concepts to optimize them for use in drawing the conclusion, and then uses the optimized concepts for drawing the conclusion.

It will be apparent that, while various embodiments are described in the context of performed automated clinical diagnosis of patients, the techniques described herein may be generalized to other applications. For example, these techniques may be used for Internet search engines or expert systems across various fields such as legal (e.g., location of applicable precedent), law enforcement (e.g., identification of suspects from description), or psychology (e.g., diagnosis of psychological condition).

FIG. 1 illustrates a system 100 for inferring a patient's diagnosis in accordance with one embodiment. As shown, the system 100 includes a processor 120, memory 130, a user interface 140, a communication interface 150, and storage 160 interconnected via one or more system buses 110. It will be understood that FIG. 1 constitutes, in some respects, an abstraction and that the actual organization of the system 100 and the components thereof may differ from what is illustrated.

The processor 120 may be any hardware device capable of executing instructions stored on memory 130 or storage 160 or otherwise capable of processing data. As such, the processor 120 may include a microprocessor, field programmable gate array (FPGA), application-specific integrated circuit (ASIC), or other similar devices.

The memory 130 may include various memories such as, for example L1, L2, or L3 cache or system memory. As such, the memory 130 may include static random access memory (SRAM), dynamic RAM (DRAM), flash memory, read only memory (ROM), or other similar memory devices.

The user interface 140 may include one or more devices for enabling communication with a user such as a patient or medical personnel. For example, the user interface 140 may include a display, a mouse, and a keyboard for receiving user commands. In some embodiments, the user interface 140 may include a command line interface or graphical user interface that may be presented to a remote terminal via the communication interface 150.

The user interface 140 may present an agent in the form of an avatar to communicate with a user. The displayed agent may of course vary and depend on the application.

The communication interface 150 may include one or more devices for enabling communication with other hardware devices. For example, the communication interface 150 may include a network interface card (NIC) configured to communicate according to the Ethernet protocol. Additionally, the communication interface 150 may implement a TCP/IP stack for communication according to the TCP/IP protocols. Various alternative or additional hardware or configurations for the communication interface 150 will be apparent.

The storage 160 may include one or more machine-readable storage media such as read-only memory (ROM), random-access memory (RAM), magnetic disk storage media, optical storage media, flash-memory devices, or similar storage media. In various embodiments, the storage 160 may store instructions for execution by the processor 120 or data upon with the processor 120 may operate.

For example, the storage 160 may include or otherwise be configured to execute various components for inferring a patient's diagnosis. As seen in FIG. 1, these components may include input handling instructions 161, concept extraction instructions 162, query formulation instructions 163, evidence search instructions 164, concept refinement agent instructions 165, agent training instructions 166, and conclusion presentation instructions 167. An example of the operation of these instructions will be described in greater detail below. As will be understood in the field of machine learning, the various instructions 162-167 may be executed at different times for different purposes such as, for example, as part of a training phase and as an operation phase. For example, the agent training instructions 166 (which may include, e.g., a reward function and instructions for implementing Q-learning) may only operate during the training phase to digest a large training set of problem statements and associated ground truths and thereby train the concept refinement agent instructions 165 for later operation. As another example, the conclusion presentation instructions 167 may only be executed during the operation phase to output the refined concepts or ultimate conclusion(s) to the user according to the purpose for which the system has been trained and deployed.

It will also be understood that in various embodiments, the training phase and operation phase may not be performed in the same location or by the same device. For example, the concept refinement agent instructions 165 may be trained in a lab setting and then deployed across other hospital systems or on a cloud-based virtual machine accessible via, e.g., a mobile app, web browser, etc. Accordingly, in some embodiments, the system 100 may omit one or more of the instructions 162-167 such as, for example, the agent training instructions 166 or conclusion presentation instructions 167. Additionally, in some embodiments, one or more instructions 162-167 may be hosted on a different device. For example, the concept refinement agent instructions 165 may be hosted on a separate device (not shown) and the remaining instructions may utilize the concept refinement agent instructions 165 as a remote service, e.g., via a RESTful API.

It will also be understood that in some embodiments, the training phase and operation phase may at least partially overlap. For example, in some embodiments, the agent may continue to learn and improve (e.g., based on human operator feedback taken as the ground truth on a case-by-case basis) even after deployment.

In some embodiments, the device 100 may be implemented as a cloud-based virtual machine. As such, the various components 120-160 may, in some embodiments, be distributed across multiple physical devices and, in some cases, may be duplicated. For example, a virtual machine may utilize two or more processors 120 in various embodiments.

Figure 2:
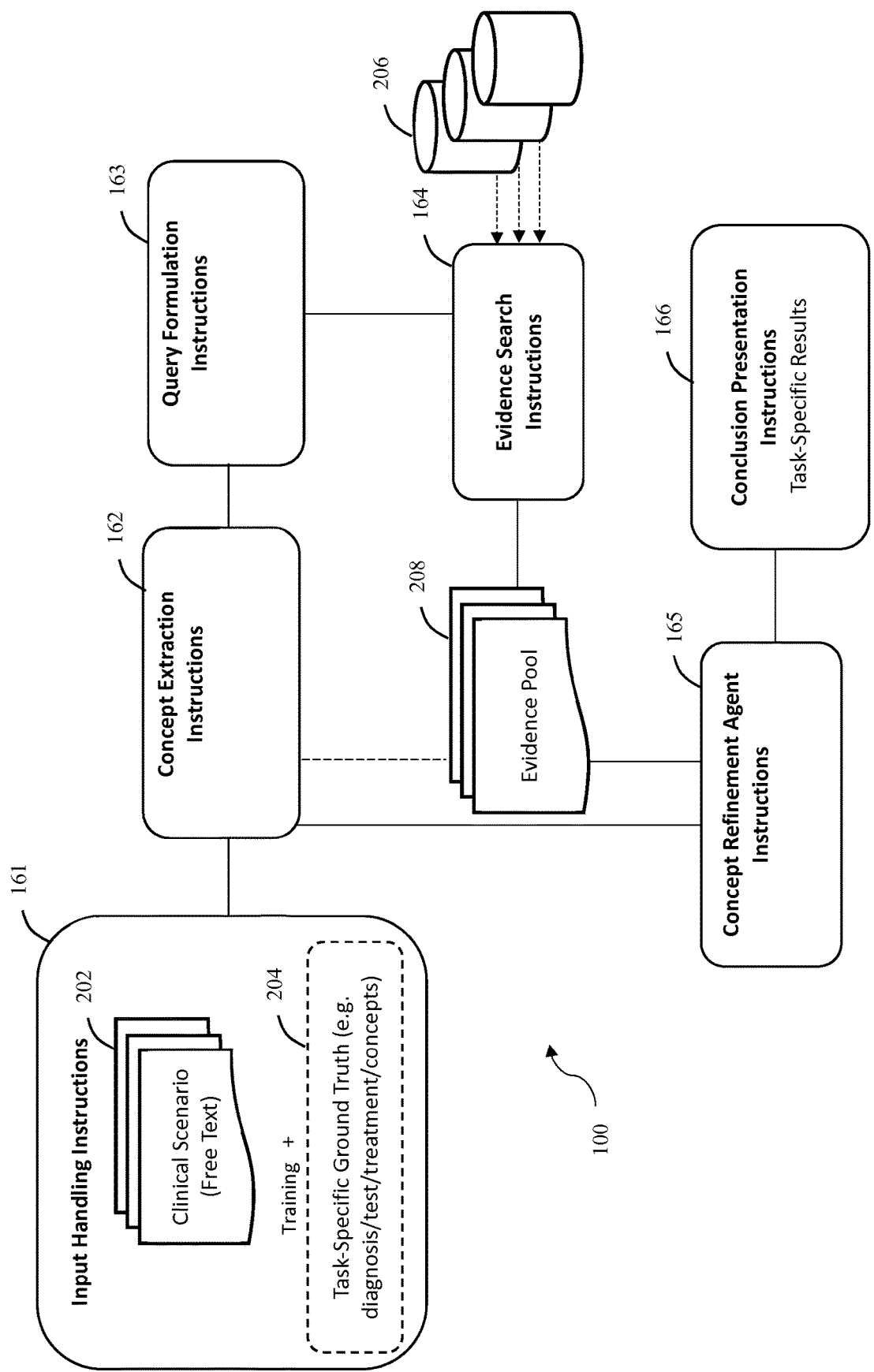
FIG. 2 illustrates the workflow of the system of FIG. 1 in accordance with one embodiment.

FIG. 2 illustrates the workflow of the system 100 in accordance with one embodiment. An input 200 such as the user interface 140, communications interface 150, or a software process (not shown) to receive data from a local or remote software process (not shown) operating as a client of the present system may present free text 202 regarding a clinical scenario. For example, the free text 202 may include notes relating to a patient's conversation with medical personnel and include the patient's description of their symptoms.

During the training phase, the input 200 may additionally provide task-specific knowledge 204 to be used for training the agent. During training, the system 100 may learn an optimal policy to take a decision for an action (e.g., accept/ reject a clinical concept) and a query to maximize an overall reward while minimizing the number of steps to reach the maximum accuracy.

Existing tools and techniques for extracting concepts from free texts mainly depend on large corpora of labeled examples and knowledge bases. Additionally, these existing tools and techniques are often limited to the original content of the text they are trained on and do not consider evidence from additional, free text resources.

Therefore, the concepts extracted by these tools often lack aspects related to in-domain normalization. This, in turn, may have a negative impact on the downstream inference task.

Similarly, concepts may be represented using different word-phrase combinations in literature. Without further processing of these concepts (e.g., paraphrasing), it can be difficult to map them to well-known concepts in a knowledge base and to infer the correct diagnosis.

The concept extraction instructions 162 may implement any one of a variety of content extraction tools to extract concepts from the text 202. According to various embodiments, a "concept" may be a group of text or other data (or representation thereof) extracted from a larger corpus of similar data. For example, the concept extraction instructions 162 may utilize the MetaMap software tool or cTAKES software tool to discover concepts referred to in text. Or, in other embodiments, the concept extraction instructions 162 may implement noun-phrase (NP)-chunking techniques (or other chunking techniques) that segment and label multi-token sequences. Specifically, NP-chunking is a technique that searches for chunks corresponding to individual noun phrases in a word sequence. In some embodiments, the concept extraction instructions 162 may leverage other information such as external resources 206 to identify which phrases or terms are to be taken as "concepts;" for example, where an external resource is a collection of linked pages, any term that is presented in an entry body as a hyperlink to another page or a dedicated entry for that phrase or term, it may be taken to be a "concept." As another example, any term listed by an ontology (e.g., MILS) may be taken as a concept. Various alternative approaches to extracting concepts from the text 202 may be employed.

The concept extraction instructions 162 may implement any sort of content extraction tools, whether available now or invented hereafter, as long as they can extract source concepts to accomplish the features of various embodiments described herein. The source concepts may then be communicated to the query formulation instructions 163.

The query formulation instructions 163 may be configured to formulate one or more queries for external resources 206. The query formulation instructions 163 may formulate these queries based on pre-defined templates or dynamically using some heuristics (e.g., based on n-grams, all concepts, all text, etc.). For example, in some embodiments, the query formulation instructions may simply form a Boolean query where each concept is joined by an AND or an OR operator. As another example, the query may be formed as an elasticsearch query. Various alternative methods for constructing queries based on textual or other types of concepts will be apparent.

The queries formulated by the query formulation instructions 163 may be executed against one or more external resources 206. In some embodiments, the external resources 206 may include remote databases or other collection of expert information such as, for example, Wikipedia, Mayo-Clinic, MIMIC, HumanDx, or the like. While the term "external resources" is used, it will be apparent that such term may encompass knowledge sources that are at least partially locally stored. For example, in some embodiments, the system may store a local cache of entries from such remote sources that may be queried. To execute the queries, the query formulation instructions 163 may also execute the queries by submitting the queries to a search engine via suitable application programming interface (APIs) such as those offered by the external resources (e.g., the built-in Wikipedia or Mayo Clinic search functionality) or by a third party service (e.g., search engines offered by Google or Bing to search the external resources). The documents returned in response to those queries may then be added to an evidence pool 208. In various embodiments, the evidence pool 208 may be a collection of search results to be used, as explained below, for extracting ideal normalized concepts to refine the initially extracted concepts or to draw conclusions for presentation to the user.

The evidence search instructions 164 may be configured to search the external resources for relevant evidence with respect to the clinical scenario. Concepts may then be similarly extracted (e.g., using the concept extraction instructions 162) from the documents in the evidence pool 208 and presented to the concept refinement agent instructions 165 along with the initially extracted concepts to begin refinement of the concepts.

Figure 3:
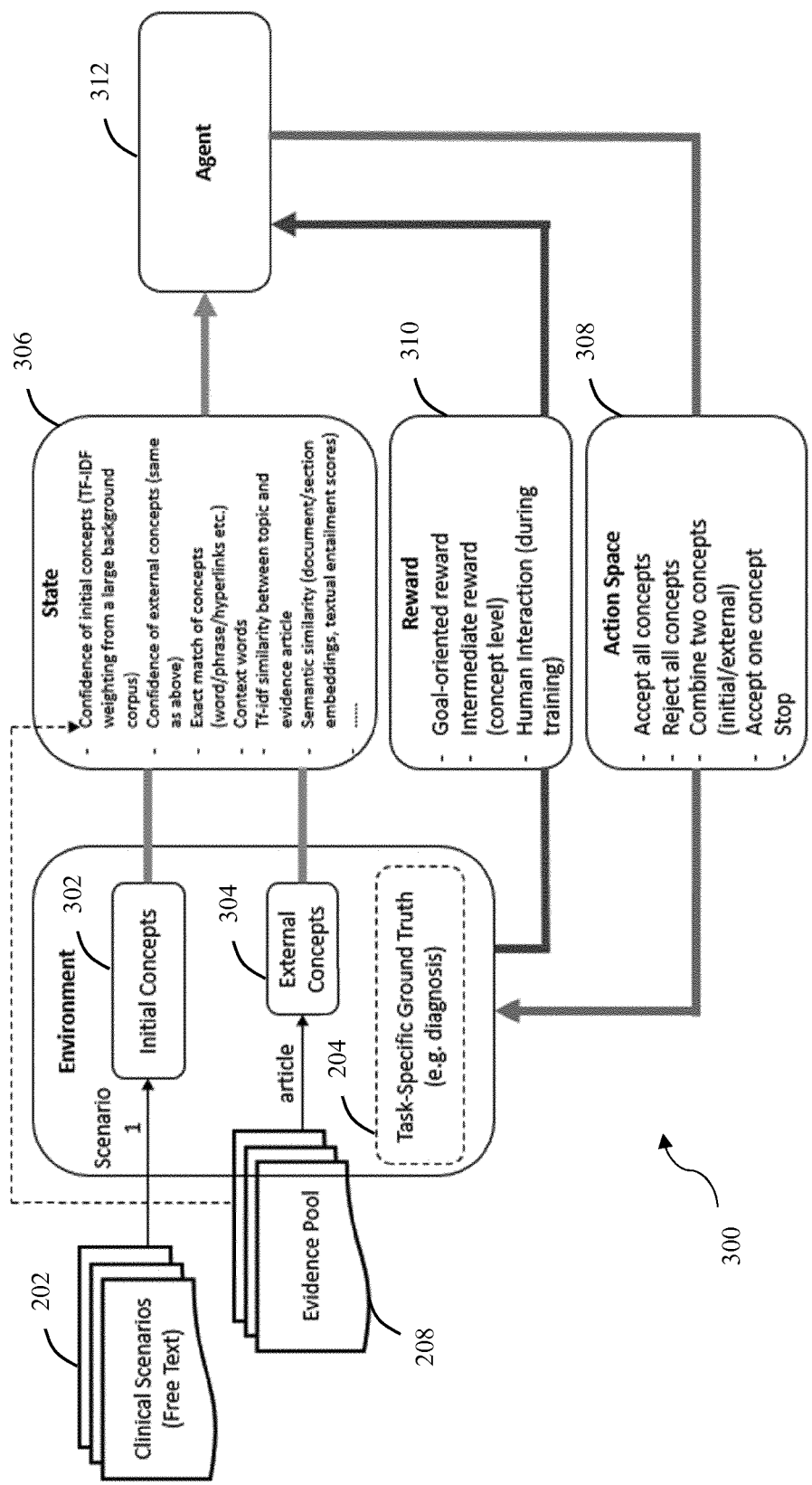
FIG. 3 illustrates the reinforcement learning framework, which may be executed by the agent training instructions of FIG. 1 in accordance with one embodiment.

The concept refinement agent instructions 165 may implement the reinforcement learning framework 300 of FIG. 3 or may be an agent previously-trained to operate according to the reinforcement learning framework 300, depending on the phase in which the system 100 is operating. As will be explained in greater detail below, the concept refinement agent instructions may generate a number of features based on comparison of the "initial concepts" and the "external concepts." That is, the initial concepts are extracted from the free text 202 and the external concepts are extracted from external documents in the evidence pool 208 (e.g., by the concept extraction instructions 162).

The reinforcement learning framework 300 may implement, for example, a Markov Decision Process (MDP) and a deep Q-network, though alternative mechanisms for implementing the approaches of extracted concept normalization described herein may be employed (e.g., a partially observable Markov decision process). Beginning with the initial concepts 302 and the external concepts 304, the MDP may encode the two sets of concepts into a state space 306. The MDP framework may also define an action space 308 of actions that the agent 312 is allowed to take at each step and a reward function 310 for gauging the desirability of the outcome for each action taken by the agent 312 at different states. At each MDP step, one external article from the evidence pool 208 may be considered based on the initial clinical concepts 302. It will be apparent that variations are possible; for example, in some embodiments, an MDP step may take multiple or all external evidences into account. For example, another process may be performed (not shown) for digesting all external evidence into a single set of external concepts 304 to be considered in a single step.

To encode the initial concepts 302 and external concepts 304 into the state space 306, the framework 300 may extract one or more features from the concepts 302, 304. For example, the state space may include a measure of the confidence in each of the concepts 302, 304 such as, for example, a term frequency-inverse document frequency (TF-IDF) metric computed for each term across the evidence pool or the external resource(s) itself. The state space 306 may include additional or alternative features such as indications of exact matches between concepts 302, 304 (i.e., concept-level matches of words, phrases, hyperlinks, etc.); embeddings of context words surrounding the extracted concepts; TF-IDF similarities between topics and articles from the pool 208; and the semantic similarity between documents, section embeddings, overall context, or the like. For example, word-, phrase-, and hyperlink-level exact matching may indicate if there is a direct overlap between the current clinical concepts and the newly extracted concepts. The state vector may also contain the TF-IDF similarity between the topics (e.g. evidence article title) and articles (content of the article) such that it can encode the overall contextual similarity of a clinical concept with the entire article content. Vector space modeling of the evidence article content and the clinical concepts may also be leveraged to represent various granularities of the content (e.g. word, phrase, context (e.g. up to window size=5 beside the clinical concept in a document), sentence, underlying section, paragraph, and the overall document-level) embeddings in order to measure semantic similarity (e.g. via cosine distance measure) between the current concepts and the newly extracted concepts and/or between underlying documents, sections, paragraphs or the overall contexts.

Figure 6:
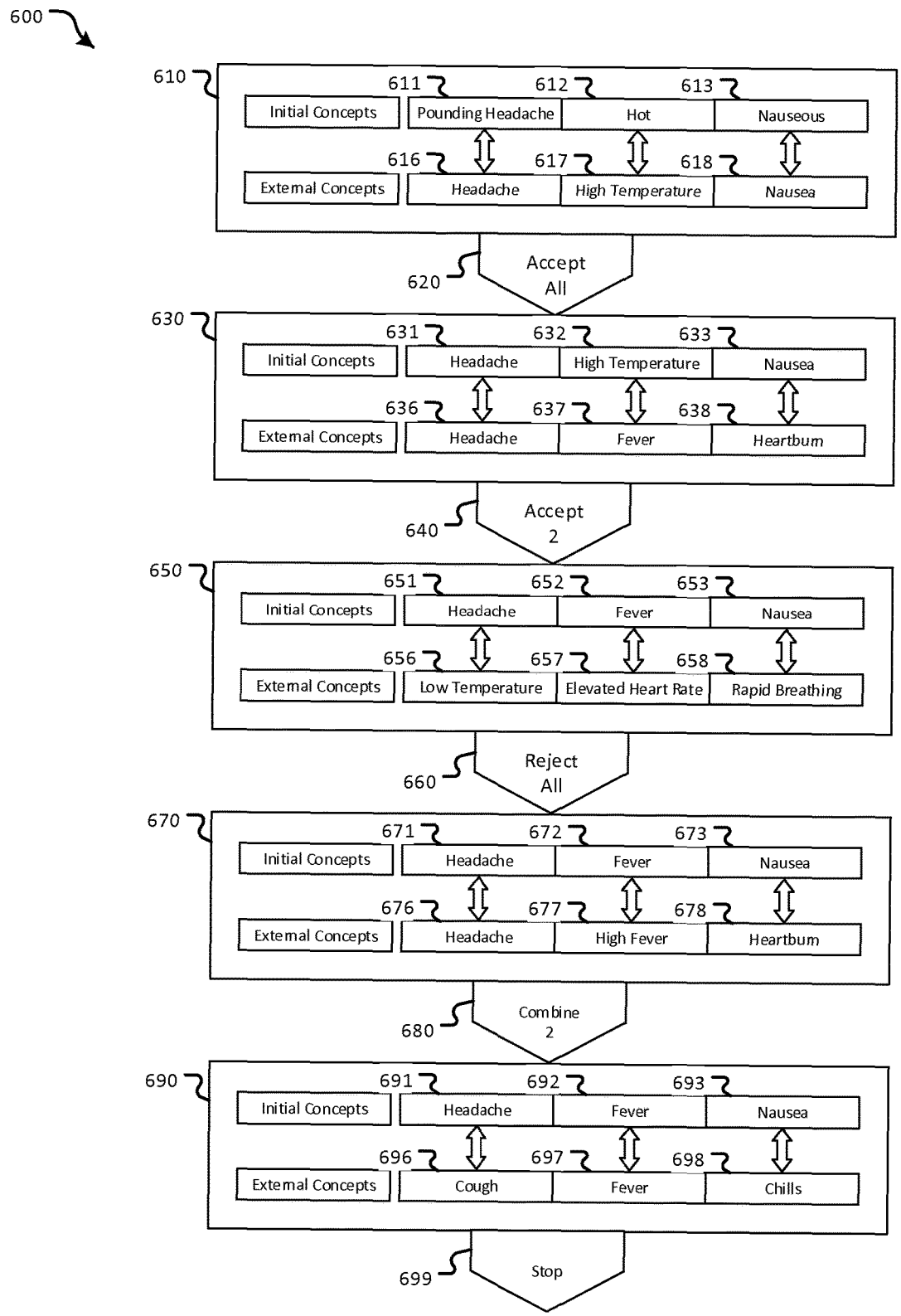
FIG. 6 illustrates an example action sequence performed by an agent for concept normalization according to various embodiments.

The action space 308 may define the actions that the agent 312 may take at a step of the MDP process. For example, with regard to the external concepts, the agent may accept one or all of the concepts to be used as initial concepts going forward, may reject all concepts and continue with the current initial concepts, combine two concepts between the internal and external concepts (e.g., where the concepts are not identical but related), or stop the process once the initial concepts are deemed sufficiently normalized against the external evidence. An example of the operation of these actions will now be described with respect to the example action sequence 600 of FIG. 6.

As shown in a first environment 610, there are three initial concepts 611, 612, and 613 (e.g., extracted from the free text if this is indeed the first iteration of the agent) and three external concepts 616, 617, 618 for consideration. In this embodiment, each of the two concept sets are provisioned with three "slots" for storing a concept and, as will be explained, each step determines whether one or more of the slots for the initial concepts will store a different concept going forward.

It will be appreciated that in various embodiments, a different number of slots may be provided. For example, there may be 10 slots for each of the internal or external concepts. In some such embodiments, the environment 610 may not begin with each of the slots filled with a concept. For example, if only two concepts are located in the input text, the third slot may be initially empty and later replaced with a concept taken from the external evidence.

Further, as shown, the slots are "paired up" between initial concept slots and external concept slots. In such embodiments, each external concept is considered at each step to be moved into the paired initial concept slot. Thus, such embodiments may not compare each external concept to each initial concept, but rather may consider each such pair. In some such embodiments, the concepts may be ordered to promote comparison between somewhat similar terms. For example, the external concept placed in slot 1 may be that concept deemed closest (e.g., by comparing word embedding) to the term currently in slot 1 of the initial concepts. Similar methodology may be followed to select concepts for the subsequent slots.

It will be apparent that various alternative embodiments may not pair the initial and external concepts up in this manner and, instead, each external concept may be compared against each initial concept for possible replacement. In such embodiments, there may be a different number of initial concept slots from the number of external concept slots. As will be explained in greater detail below, such an embodiment may be accommodated by an expansion of the action space.

Following the example action sequence 600, the agent first considers the initial concepts {Pounding Headache, Hot, Nauseous} against the external concepts {Headache, High Temperature, Nausea}. Given this environment (and state extracted therefrom, not shown), the agent has selected the "Accept All" action 620. According to this action, each external concept 616, 617, 618 replaces the corresponding concept in the initial concepts slots 611, 612, 613. Thus, the resulting environment 630 includes a new list of initial concepts 631, 632, 633 {Headache, High Temperature, Nausea}.

This next environment 630 also presents a new list of external concepts 636, 637, 638 to be considered, {Headache, Fever, Heartburn}. These new concepts may be extracted from another piece of evidence in the pool, which may have been updated in response to the previous action 620. For example, whenever an action results in a change to the initial concepts (e.g., as in the case of the Accept All action 620), the system (e.g., the query formulation instructions 163, evidence search instructions 164, and concept extraction instructions 162) may update the evidence pool based on the new concepts.

In considering the external concepts 636, 637, 638, the agent may decide that only the second slot presents a more desirable concept and, as such, chooses the Accept 2 action 640. The resulting environment 650 may thus include updated initial concepts slots 651, 652, 653 that includes a new concept in only slot 652. To accommodate selection of any of the individual slots in this manner, the action space may include multiple "Accept One" actions. In this example, there may be one such action for each pair of slots: Accept 1, Accept 2, and Accept 3. More generally, for an environment including N pairs of concept slots, the action space may include N "Accept One" actions in addition to the other actions described herein. Following this concept, it will be apparent that various embodiments may enable acceptance of multiple slots but fewer than all slots. For example, the action space may be expanded to include "Accept 1&2" "Accept 1&3" and "Accept 2&3" In embodiments that enable the comparison of all initial concepts to all external concepts, the action space may be expanded to include N*M new "Accept One" actions, where N is the number of initial concept slots and M is the number of external concept slots. Such additional actions may include, for example, Accept 1 into slot 1, Accept 1 into slot 2, etc.

At the next environment 650, the agent may view the new set of external concepts 656, 657, 658 and determine that none propose a desirable alternative to any of the initial concepts 651, 652, 653 and therefore choose the Reject All action 660. Thereafter, the initial concepts 671, 672, 673 of the new environment are unchanged while a new set of external concepts 676, 677, 678 are presented. Viewing these concepts, the agent may determine that the concepts in slot 2, "Fever" and "High Fever" are sufficiently close to be combined into a single concept and therefore choose the "Combine 2" action 680. As with the "Accept N" actions, the action space may be expanded to account for "Combine N" actions to be performed on any of the slot pairs such as, in the present example "Combine 1," "Combine 2," and "Combine 3." Additional expansions of the action space (e.g., for full pairwise comparison of all concepts or for combination of multiple slot pairs in one step) may also be possible in a manner similar to the described above.

As a result of the Combine 2 action 680, the agent has combined the concepts of "High Fever" and "Fever" into the single concept of "Fever" in the resulting environment 690. In other words, the agent has identified the more general term ("Fever") and selected it to be stored in slot 2 692. According to various embodiments, unlike the Accept/Reject actions, the Combine action may operate regardless of whether the more generic term was located in the initial concept or external concept slot. In other words, has slot 672 stored the "High Fever" concept and slot 677 stored the "Fever" concept, the result of the combine 2 action would still have been to store the "Fever" concept in initial concept slot 2 692. Thus, for similar or overlapping concepts, the agent need not determine whether the external or initial concept is broader in order to decide to accept or reject, but can rather elect to combine. A process in the environment may then interpret the combine action using a different process such as, for example, mapping the concepts to an ontology and selecting the one closer to the root. Alternatively, the agent may decide to include "High Fever" as the modified concept based on its choice to include more specific information, which might help it to reduce the number of steps to reach an optimum conclusion (i.e. the diagnosis) based on maximum gained rewards in the future.

In various alternative embodiments or situations, the "combine" action may have a slightly different effect. For example, rather than selecting the more generic, the slot may be occupied by a search string including both concepts, such that both are located when used in a query. In such embodiments, for example, the agent may decide to combine the concepts "Fever" and "Sweating", resulting in the concept "(Fever OR Sweating)" being stored in a single concept slot.

In the final environment, the agent may compare the initial (to that step) concepts 691, 692, 693 to the new external concepts 696, 697, 698 and determine that the initial concepts 691 are now suitably normalized and choose the stop action 699. These initial concepts 691, 692, 693 may thereafter be presented as the output of the decision process and used for downstream processing. For example, these concepts may be used to search the external resources 206 or evidence pool 208 one more time to retrieve a list of entries to serve as diagnoses (or other conclusions in non-clinical settings). Various other uses for and associated options for downstream processing of such normalized extracted concepts will be apparent.

Returning to FIG. 3, the reward function 310 is discussed in more detail below and can be a goal-oriented reward (which is based on the accuracy of diagnosis or other conclusion outputs) or an intermediate reward (which is based on the accuracy of the extracted and normalized concepts). In some embodiments, the reward function aggregates both the goal-oriented and intermediate rewards. Additionally or alternatively, the reward function can also consider human feedback. The reward function 310 may be used during training of the agent 312 to determine the desirability of an outcome of an action chosen by the agent 312 and to modify the agent 312 and learn therefrom.

For a given clinical scenario (or other textual or other data input), the agent 312 extracts the set of initial concepts 302 which are used to generate the queries. A new state s is generated that may include the agent's confidence in the current concepts or other features such as those described above with respect to the state space 306. In a state s, the agent 312 may select an action a to be performed (e.g., by a process overseeing the environment) to get to the next state s' (as will be determined from the updated environment after execution of the selected action).

During the training phase, the reward function r(s, a) 310 computes a reward according to some formula based on the outcome of each action selected by the agent. An example of such a reward function will be described in detail below. The reward may be computed, for example, every time the agent 312 selects an action and the environment process updates the environment in accordance with that action (e.g., by changing the initial concepts 302). The rewards delivered by the reward function 310 may be used by a reinforcement learning algorithm during the training phase (or during the operation phase when dynamic learning is implemented) to train the agent to choose those actions most likely to lead to a high reward for any given state. For example, some embodiments may implement deep Q-learning, as will be explained in greater detail below. Such embodiments may implement a state action value function Q(s, a) that is trained to return a score for action a to be performed in state s. The action a with the highest Q-score may thus be selected by the agent 312.

According to one example for a clinical diagnosis application, the MDP may be carried by the following procedure:

reward function may consider a goal-oriented reward $r_{goal}$ that reflects the accuracy of the conclusion that will be drawn (e.g., by a downstream process) from the normalized concepts. Such accuracy may be gauged by comparing the ground truth to the conclusion to be drawn (or to a ranked list of conclusions to be drawn). Second the reward function 310 may consider an intermediate or concept-level reward $r_{inter}$ that evaluates the accuracy of extracted concepts. Considering both types of rewards, the reward function may be written as:

$$r = w \times r_{goal} + (1-w) \times r_{inter} \quad \text{(Eq. 1)}$$

where w is the weight factor which is empirically set to assign importance to a certain type of reward. In some embodiments in which both rewards are used, w may be set to, e.g., w=0.9. A set of clinical concepts C may be used as

```
Input: Clinical narratives N = {N₁, N₂,..., Nₙ}
Output: Improved clinical concepts Cᵢᶜᵘʳ towards correct diagnosis for each Nᵢ.
for each clinical narrative {
    Retrieve top K Wikipedia articles Y₀;
    Retrieve top K MayoClinic articles Y₁;
}
for Nᵢ, in N do
    Extract entities C from Nᵢ;
    Cᶜᵘʳ ← C;
    q ← 0, r ← 0 //query type, reward;
    for i = 1, K do
        Pop next article y from Y_q;
        Extract entities Cⁿᵉʷ from Y_q;
        Generate state vector v based on comparison between Cᶜᵘʳ and Cⁿᵉʷ;
        Send (v, r) to DQN agent, and get actions q and d from agent;
        if action d = = "stop" then break;
        Update Cᶜᵘʳ according to d;
            Update the value of q; // may determine which resource pool should be used
to query (for this example, it may be 0 or 1, denoting Wikipedia or Mayo, respectively)
        Calculate reward value r;
        end
        Send (v, r) to DQN agent.
end
```

The framework 300 of FIG. 3 is tasked to find a set of appropriate clinical concepts and a correct diagnosis. The framework 300 considers each state s as a continuous real-valued vector including a set of current clinical concepts $C^{cur} = \{c_1^{cur}, \ldots, c_N^{cur}\}$ and a set of new concepts $C^{new} = \{c_1^{new}, \ldots, c_N^{new}\}$ extracted from an external article. The current and new clinical concepts may be aligned as: (1) an exact match between current and new concepts; (2) high similarity match based on clinical phrase embedding-based similarity score; and (3) direct alignment to a current null value.

The state space 306 vector essentially represents the similarity between the current clinical concept set $C^{cur}$ and the new concept $C^{new}$ including their context in the external article. The state vector may encode information about the current and new concepts based on: (1) confidence values of current concepts; (2) confidence values of external concepts; (3) matching scores between current and new concepts calculated by exploiting a phrase embedding model; and (4) tf-idf similarity between the current and new context.

At each state, the agent 312 may output an action. The agent may, for example, accept all new clinical concepts, reject all new clinical concepts, accept one new clinical concept, combine a pair of concepts, or stop the routine entirely.

The reward function 310 in accordance with various embodiments considers two types of rewards. First, the the queries to search the external resources and to retrieve a ranked list of possible candidate diagnoses.

According to the rank of the correct conclusions (as determined by downstream processing, such as an additional query to the external resources) among the candidate list, the framework 300 may return a Mean Reciprocal Rank (MRR) score. $r_{goal}$ is computed by: $r_{goal} = MRR_C^{new} - MRR_C^{cur}$ where $MRR_C = 1/\text{rank}_C$ and $\text{rank}_C$ represents the rank of the correct conclusion among the list of candidate conclusions when the concept set C is used as the search queries.

In some embodiments, an external resource (e.g. the HumanDx resource) may be referenced to compute the intermediate reward, $r_{inter}$. In some embodiments, this external resource may be different from the external resource(s) used during the concept normalization process. The ground truth conclusion may be used to search the external resource to obtain a list of associated clinical concepts. For a clinical concept set C, the framework 300 may count the number of concepts ($N_c$) that occur in the HumanDx concept set. Thus, the intermediate reward is computed by the number of new concepts that occur in external resource minus the number of current concepts that occur in the external resource: $r_{inter} = |N_C^{new} \cap N_C^{cur}|$.

Figure 4:
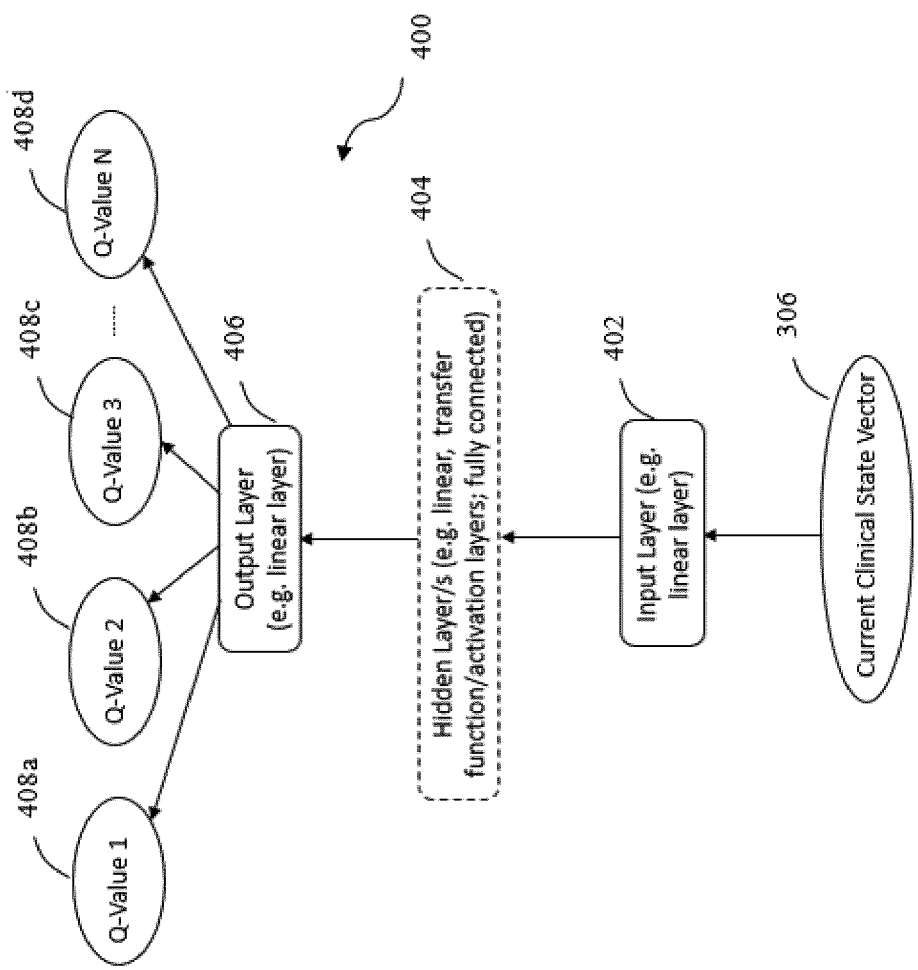
FIG. 4 illustrates the Q learning framework executed by the agent training instructions of FIG. 1 in accordance with one embodiment.

In order to learn the Q value, the iterative updates may be obtained from the Bellman equation:

$$Q_{i+1}(s,a) = E[r + \gamma \max_{a'} Q_i(s',a')|s,a] \quad \text{(Eq. 2)}$$

where γ is the discount factor for the future rewards and the expectation is over the whole training process. Some embodiments may opt not to maintain Q-values for all possible state-action pairs. Accordingly, methods and systems of various embodiments may instead implement a Q learning framework, such as the Q-learning framework 400 of FIG. 4. Based on the state space vector 306 and layers 402-406 thereof, the Q learning framework 400 may output the Q-values 408$a$-408$d$ with the maximum future reward values for each possible action taken in the current state.

In particular, as depicted, the Q-learning framework 400 is a neural network that includes an input layer 402 of one or more nodes that accept the current state vector 306 as an input, one or more hidden layers 404 of one or more nodes each, and an output layer 406 of one or more nodes. In various embodiments, the hidden layers 404 may include multiple diverse layers (e.g., linear, transfer function/activation layers, fully connected layers, etc.) and, as such, the framework 400 may be a deep learning network. The output layer may output Q-Values 408$a$-$d$ for each possible action. For example, the Q-Values may be an estimate of a reward for taken each possible action given the input state. According to some embodiments, Q-Value 1 408$a$ may correspond to, for example, at "Accept All" action, Q-Value 2 408$b$ may correspond to the "Accept 1" action, Q-Value 2 408$b$ may correspond to the "Accept 2" action, and so on. In operation, when presented with a given state, the agent may perform a feedforward pass of the framework 400, identify the highest Q value output, and select the action corresponding to that output slot to return to the environment.

Various methods for training the Q-learning framework 400 will be apparent. For example, according to various embodiments, given a particular transition <s, a, r, s'>from state s to state s' based on action a and resulting in reward r, the learning algorithm may first perform a feedforward pass for state s to get predicted Q-values for all actions, and then perform a feedforward pass for the next state s' to determine the maximum Q-value among all the potential next actions, $\max_a Q_i(s', a')$. Next, the learning algorithm sets the Q target for the selected action a equal to $r + \gamma \max_a Q_i(s', a')$. Leaving the Q-values of all other actions the same as their output in the first step, the learning algorithm then performed a back propagation pass to update the weights at each layer 402, 404, 406, and thereby update the network 400. After many iterations of this process based on a training set of free text and associated ground truths, the network may be trained to select an optimal action for each step of the MDP.

Various alternative architectures and appropriate modification for enabling such will be apparent. For example, in some embodiments, a single framework 400 with only a single Q-value output may be provided. In such an embodiment, an action may be provided along with the state as input. To select an appropriate action, the agent may perform a separate feedforward pass for the state, s, with every possible action as input and select the action with the highest output. As yet another alternative, a separate framework 400 having a single Q-value output may be trained for each possible action.

Referring back to FIG. 2, the conclusion presentation instructions 166 may supply (e.g., to a local client process or via the user interface 140 or network interface 150) a result to a user (e.g., an administrator or medical personnel in clinical applications). The type of output may vary and may depend on the application. For example, in some embodiments, the output may be an inferred diagnosis for a patient or a ranked list of possible diagnoses for the patient. Such diagnosis or other conclusion (or ranked list thereof) may be obtained, for example, by querying the external resources using the final set of normalized concepts and selecting the top result(s) as the conclusion. Various other downstream methods for processing the list of normalized concepts will be apparent.

Figure 5:
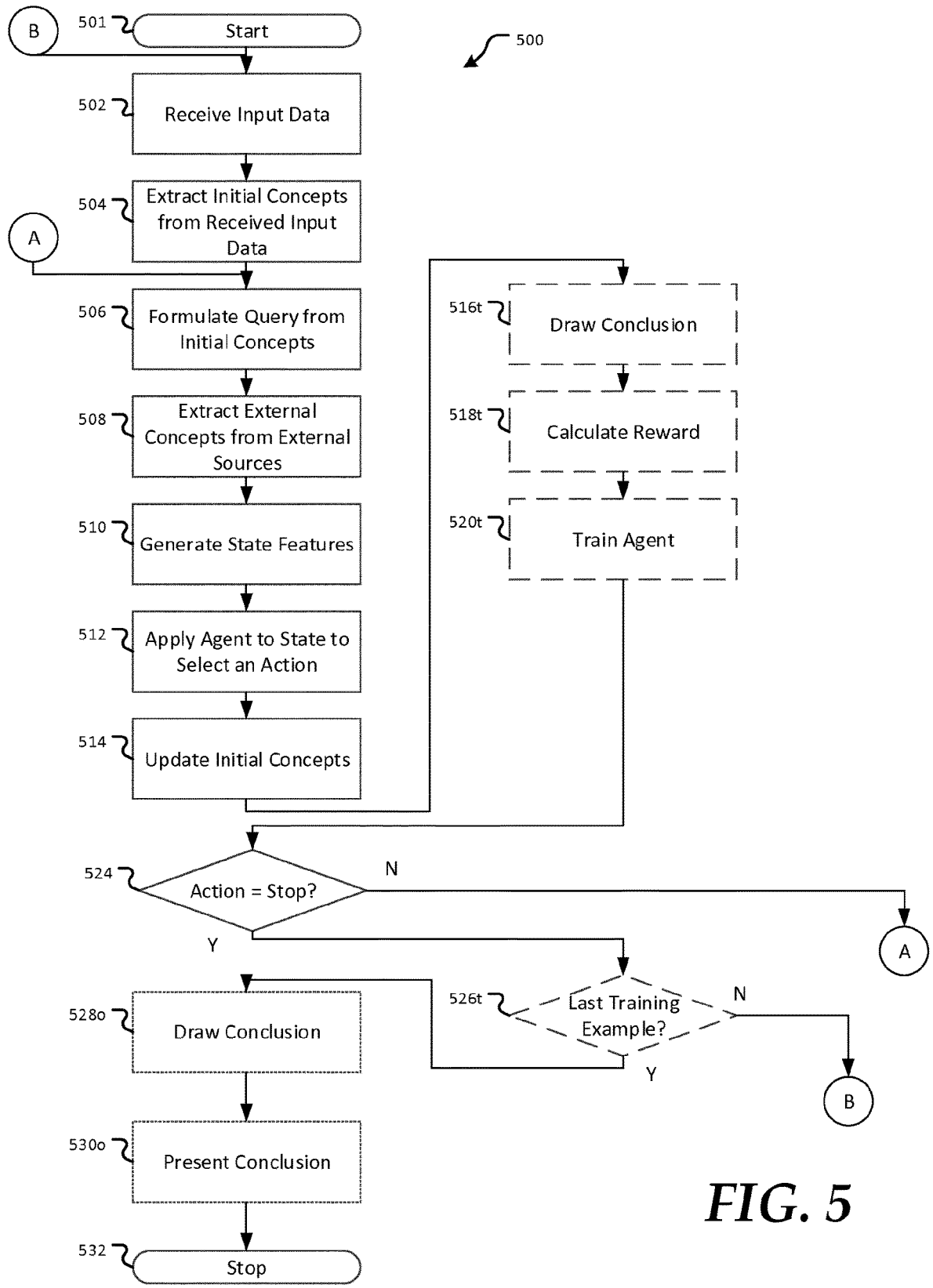
FIG. 5 depicts a flowchart of a method for inferring a patient's diagnosis in accordance with one embodiment.

FIG. 5 depicts a flowchart of a method 500 for inferring a patient's diagnosis in accordance with one embodiment. The method 500 may correspond, for example, to the various instructions 161-167 stored in the storage 160 of the system 100. Step 502 involves receiving input data, using an interface, such as text describing a patient's state. In some embodiments, the text may be raw text clinical notes that are related to a patient's medical condition. For example, the notes may be written by medical personnel after listening to a patient's symptoms or complaints.

Step 504 involves extracting at least one initial concept from the received input data. The concept may be related to the patient's state. The concept extraction module may be similar to the concept extraction module 162 of FIG. 1. Step 506 involves formulating at least one query for submission to at least one external resource, wherein the at least one query is based on the at least one initial concept. In some embodiments, formulating the query involves generating a semantically similar query using the at least one initial concept and a corpus of related medical concepts. Step 508 involves extracting at least one new concept from a response from the at least one external resource to the at least one query. Step 510 involves generating at least one feature based on a comparison of the at least one initial concept and the at least one new concept.

In step 512, the method 500 applies an agent (e.g., an already-trained agent in operation phase and an agent presently being trained in the training phase) to the generated state features to receive an indication of an action to be performed. Next, in step 514, the method 500 updates the initial concepts as indicated by the action, e.g., as described above with respect to various available actions for the agent. For example, if the agent selected the "Accept all" action, then the method 500 may replace all of the initial concepts with the external concepts in step 514.

Where the method 500 is a method for training the agent, the method 500 proceeds to draw a conclusion based on the current intermediate initial concepts list in step 516$t$. For example, the method 500 may again query the external resource and take the top result(s) to constitute the conclusion to be drawn. In step 518$t$, the method computes a reward for the selected action based on comparing the current initial concepts or the selected conclusion(s) to a ground truth received with the input data in step 504. The method 500 then proceeds to train the agent using this reward in step 520$t$, e.g., as described above using back-propagation.

In step 524, the method 500 determines whether the action selected by the agent is the "stop" action. If not, the method loops back to step 506 to continue processing another set of external concepts in the manner described above. Otherwise, if the method 500 is for execution during the training phase, it proceeds to step 526$t$ where the method 500 determines whether the current training example is the last one to be considered by the agent for training. If not, the method 500 loops back to step 502 to receive and learn from the next training example. Once all training examples have been considered, the method 500 proceeds, e.g., to end in step 532.

Where the method 500 is for execution during an operation phase, the method draws a conclusion (e.g., substantially as described above with respect to step 516*t* for the training phase) in step 528*o* and presents that conclusion (e.g., to a user or client application) in step 530*o*. The method then proceeds to end in step 532.

According to the foregoing, various embodiments present an improved method for normalizing input data prior to its use in an expert system or for another task. In particular, by iteratively challenging concepts extracted from the input against concepts similarly extracted from a knowledgebase, those concepts may be refined and normalized to match the data norms of that knowledgebase. Such an approach is particularly useful when the downstream processing of the normalized input utilizes the same knowledgebase (or one that conforms to the same data norms) for its independent function because the input has already been adapted to those specific data norms. Various additional benefits will be apparent in view of the foregoing.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of various implementations or techniques of the present disclosure. Also, a number of steps may be undertaken before, during, or after the above elements are considered.

Having been provided with the description and illustration of the present application, one skilled in the art may envision variations, modifications, and alternate embodiments falling within the general inventive concept discussed in this application that do not depart from the scope of the following claims.

What is claimed is:

1. A method for normalizing input data against external data, the method comprising:
    extracting a first concept from input data presented for processing by a downstream function;
    identifying external data from an external resource based on the first concept;
    extracting a second concept from the external data;
    revising the first concept based on the second concept to produce a revised concept, wherein revising comprises:
        applying a machine learning agent to determine whether to keep the first concept or adopt the second concept, and
        adopting the second concept in place of the first concept for use as the revised concept based on a decision by the machine learning agent to adopt the second concept;
    identifying additional external data from the external resource based on the second concept;
    extracting a third concept from the additional external data;
    applying the machine learning agent to determine whether to keep the second concept or adopt the third concept;
    adopting the third concept in place of the second concept for use as the revised concept based on a decision by the machine learning agent to adopt the third concept wherein the first, second and third concepts each indicate a symptom of a patient;
    further processing the revised concept according to the downstream function to generate an output wherein the output indicates a medical diagnosis of the patient;
    training the machine learning agent by comparing the output to a ground truth associated with the input data; and
    calculating a reward value that is used in the training of the machine learning agent.

2. The method of claim 1, wherein the input data is free text and the first concept is at least one of a term and a phrase extracted from the free text.

3. The method of claim 1, wherein identifying external data from an external resource based on the first concept comprises executing a query comprising the first concept against the external resource.

4. The method of claim 1, wherein further processing the revised concept according to the downstream function to generate an output comprises:
    executing a query comprising the revised concept against the external resource to retrieve a result; and presenting the result as the output.

5. The method of claim 1, wherein the machine learning agent comprises a deep learning neural network comprising:
an input layer that receives a state feature vector derived from the first concept and the second concept; and
an output layer that presents a plurality of expected reward values respectively associated with each of a plurality of actions, wherein the machine learning agent is configured to select one of the plurality of actions that is associated with the highest expected reward value.

6. A system for normalizing input data against external data, the method comprising:
a memory; and
a processor configured to:
extract a first concept from input data presented for processing by a downstream function;
identify external data from an external resource based on the first concept;
extract a second concept from the external data;
revise the first concept based on the second concept to produce a revised concept, wherein revising comprises:
apply a machine learning agent to determine whether to keep the first concept or adopt the second concept, and
adopt the second concept in place of the first concept for use as the revised concept based on a decision by the machine learning agent to adopt the second concept;
identify additional external data from the external resource based on the second concept;
extract a third concept from the additional external data;
apply the machine learning agent to determine whether to keep the second concept or adopt the third concept;
adopt the third concept in place of the second concept for use as the revised concept based on a decision by the machine learning agent to adopt the third concept wherein the first, second and third concepts each indicate a symptom of a patient;
further process the revised concept according to the downstream function to generate an output wherein the output indicates a medical diagnosis of the patient;
train the machine learning agent by comparing the output to a ground truth associated with the input data; and
calculate a reward value that is used in the training of the machine learning agent.

7. The system of claim 6, wherein the input data is free text and the first concept is at least one of a term and a phrase extracted from the free text.

8. The system of claim 6, wherein in identifying external data from an external resource based on the first concept the processor is configured to execute a query comprising the first concept against the external resource.

9. The system of claim 6, wherein in further processing the revised concept according to the downstream function to generate an output the processor is configured to:
execute a query comprising the revised concept against the external resource to retrieve a result; and
present the result as the output.

10. The system of claim 6, wherein the machine learning agent comprises a deep learning neural network comprising:
an input layer that receives a state feature vector derived from the first concept and the second concept; and
an output layer that presents a plurality of expected reward values respectively associated with each of a plurality of actions,
wherein the machine learning agent is configured to select one of the plurality of actions that is associated with the highest expected reward value.

11. A non-transitory machine-readable medium encoded with instructions for execution by a processor, the non-transitory machine-readable medium comprising:
instructions extracting a first concept from input data presented for processing by a downstream function;
instructions identifying external data from an external resource based on the first concept;
instructions extracting a second concept from the external data;
instructions revising the first concept based on the second concept to produce a revised concept, wherein revising comprises:
instructions applying a machine learning agent to determine whether to keep the first concept or adopt the second concept, and
instructions adopting the second concept in place of the first concept for use as the revised concept based on a decision by the machine learning agent to adopt the second concept;
instructions identifying additional external data from the external resource based on the second concept;
instructions extracting a third concept from the additional external data;
instructions applying the machine learning agent to determine whether to keep the second concept or adopt the third concept;
instructions adopting the third concept in place of the second concept for use as the revised concept based on a decision by the machine learning agent to adopt the third concept wherein the first, second and third concepts each indicate a symptom of a patient;
instructions further processing the revised concept according to the downstream function to generate an output wherein the output indicates a medical diagnosis of the patient;
instructions training the machine learning agent by comparing the output to a ground truth associated with the input data; and
instructions calculating a reward value that is used in the training of the machine learning agent.

12. The non-transitory machine-readable medium of claim 11, wherein the instructions for identifying external data from an external resource based on the first concept comprise instructions for executing a query comprising the first concept against the external resource.

13. The non-transitory machine-readable medium of claim 11, wherein the instructions for further processing the revised concept according to the downstream function to generate an output comprise:
instructions for executing a query comprising the revised concept against the external resource to retrieve a result; and
instructions for presenting the result as the output.

14. The non-transitory machine-readable medium of claim 11, wherein the machine learning agent comprises a deep learning neural network comprising:
an input layer that receives a state feature vector derived from the first concept and the second concept; and
an output layer that presents a plurality of expected reward values respectively associated with each of a plurality of actions, wherein the machine learning agent is configured to select one of the plurality of actions that is associated with the highest expected reward value.

\* \* \* \* \*